(12) United States Patent
Hayden

(10) Patent No.: US 9,322,060 B2
(45) Date of Patent: Apr. 26, 2016

(54) METHODS AND APPARATUS TO SEQUENCE A NUCLEIC ACID

(71) Applicant: Abbott Molecular Inc., Des Plaines, IL (US)

(72) Inventor: Mark A. Hayden, Ingleside, IL (US)

(73) Assignee: ABBOTT MOLECULAR, INC., Des Plaines, IL (US)

( * ) Notice: Subject to any disclaimer, the term of this patent is extended or adjusted under 35 U.S.C. 154(b) by 0 days.

(21) Appl. No.: 14/055,634

(22) Filed: Oct. 16, 2013

(65) Prior Publication Data

US 2014/0106360 A1 Apr. 17, 2014

Related U.S. Application Data

(60) Provisional application No. 61/741,789, filed on Oct. 16, 2012.

(51) Int. Cl.
C12Q 1/68 (2006.01)

(52) U.S. Cl.
CPC .................................. C12Q 1/6869 (2013.01)

(58) Field of Classification Search
None
See application file for complete search history.

(56) References Cited

U.S. PATENT DOCUMENTS

| | | | |
|---|---|---|---|
| 6,130,073 A | 10/2000 | Eggerding | |
| 6,210,891 B1 | 4/2001 | Nyren et al. | |
| 6,258,568 B1 | 7/2001 | Nyren | |
| 6,818,395 B1 | 11/2004 | Quake et al. | |
| 6,833,246 B2 | 12/2004 | Balasubramanian | |
| 6,911,345 B2 | 6/2005 | Quake et al. | |
| 6,969,488 B2 | 11/2005 | Bridgham et al. | |
| 7,115,400 B1 | 10/2006 | Adessi et al. | |
| 7,169,560 B2 | 1/2007 | Lapidus et al. | |
| 7,170,050 B2 | 1/2007 | Turner et al. | |
| 7,282,337 B1 | 10/2007 | Harris | |
| 7,302,146 B2 | 11/2007 | Turner et al. | |
| 7,313,308 B2 | 12/2007 | Turner et al. | |
| 7,315,019 B2 | 1/2008 | Turner et al. | |
| 7,329,492 B2 | 2/2008 | Hardin et al. | |
| 7,405,281 B2 | 7/2008 | Xu et al. | |
| 7,476,503 B2 | 1/2009 | Turner et al. | |
| 7,482,120 B2 | 1/2009 | Buzby et al. | |
| 7,501,245 B2 | 3/2009 | Quake et al. | |
| 7,668,697 B2 | 2/2010 | Volkov et al. | |
| 7,935,822 B2 | 5/2011 | Arden-Jacob et al. | |
| 8,612,161 B2 | 12/2013 | Gordon et al. | |
| 2001/0044109 A1* | 11/2001 | Mandecki | ................... 435/6 |
| 2003/0003486 A1 | 1/2003 | Sauer et al. | |
| 2006/0179585 A1 | 8/2006 | Zilles et al. | |
| 2007/0036511 A1 | 2/2007 | Lundquist et al. | |
| 2007/0072196 A1 | 3/2007 | Xu et al. | |
| 2007/0077564 A1 | 4/2007 | Roitman et al. | |
| 2007/0128133 A1 | 6/2007 | Eid et al. | |
| 2007/0134128 A1 | 6/2007 | Korlach | |
| 2007/0141598 A1 | 6/2007 | Turner et al. | |
| 2007/0161017 A1 | 7/2007 | Eid et al. | |
| 2007/0188750 A1 | 8/2007 | Lundquist et al. | |
| 2007/0196846 A1 | 8/2007 | Hanzel et al. | |
| 2007/0206187 A1 | 9/2007 | Lundquist et al. | |
| 2007/0231804 A1 | 10/2007 | Korlach et al. | |
| 2007/0238679 A1 | 10/2007 | Rank et al. | |
| 2008/0009007 A1 | 1/2008 | Lyle et al. | |
| 2008/0030628 A1 | 2/2008 | Lundquist et al. | |
| 2008/0032301 A1 | 2/2008 | Rank et al. | |
| 2008/0050747 A1 | 2/2008 | Korlach et al. | |
| 2008/0080059 A1 | 4/2008 | Dixon et al. | |
| 2008/0095488 A1 | 4/2008 | Foquet et al. | |
| 2008/0108082 A1 | 5/2008 | Rank et al. | |
| 2008/0128627 A1 | 6/2008 | Lundquist et al. | |
| 2008/0145278 A1 | 6/2008 | Korlach | |
| 2008/0152280 A1 | 6/2008 | Lundquist et al. | |
| 2008/0152281 A1 | 6/2008 | Lundquist et al. | |
| 2008/0153095 A1 | 6/2008 | Williams et al. | |
| 2008/0153100 A1 | 6/2008 | Rank et al. | |
| 2008/0157005 A1 | 7/2008 | Lundquist et al. | |
| 2008/0160531 A1 | 7/2008 | Korlach | |
| 2008/0165346 A1 | 7/2008 | Lundquist et al. | |

(Continued)

OTHER PUBLICATIONS

Dressman D, Yan H, Traverso G, Kinzler KW, Vogelstein B. Transforming single DNA molecules into fluorescent magnetic particles for detection and enumeration of genetic variations. Proc Natl Acad Sci U S A. Jul. 22, 2003; 100(15):8817-22. Epub Jul. 11, 2003.*

Kartalov EP, Quake SR. Microfluidic device reads up to four consecutive base pairs in DNA sequencing-by-synthesis. Nucleic Acids Res. May 20, 2004; 32(9):2873-9.*

Shendure J, Porreca GJ, Reppas NB, Lin X, McCutcheon JP, Rosenbaum AM, Wang MD, Zhang K, Mitra RD, Church GM. Accurate multiplex polony sequencing of an evolved bacterial genome. Science. Sep. 9, 2005; 309(5741):1728-32. Epub Aug. 4, 2005.*

Shendure et al. Supplementary information. Science. Sep. 9, 2005; 309(5741):1728-32. Epub Aug. 4, 2005.*

(Continued)

*Primary Examiner* — Samuel Woolwine
*Assistant Examiner* — Olayinka Oyeyemi
(74) *Attorney, Agent, or Firm* — David A. Casimir; Casimir Jones, S.C.

(57) ABSTRACT

Methods, systems, apparatus and machine readable media are disclosed to sequence nucleic acid. An example method includes subjecting a sequence of target nucleotide bases captured on a microtransponder to a plurality of sequencing reactions to build a sequence of labeled nucleotide bases that are complementary to and bound to the sequence of target nucleotide bases. The example method also includes identifying each labeled nucleotide base of the sequence of labeled nucleotide bases and each respective complementary target nucleotide base of the sequence of target nucleotide bases to which the labeled nucleotide base is bound after each sequencing reaction. In addition, each labeled nucleotide base of the sequence of labeled nucleotide bases and each respective complementary target nucleotide base of the sequence of target nucleotide bases to which the labeled nucleotide base is bound is associated with a microtransponder identification number.

18 Claims, 5 Drawing Sheets

(56) References Cited

U.S. PATENT DOCUMENTS

| | | |
|---|---|---|
| 2008/0176241 A1 | 7/2008 | Eid et al. |
| 2008/0176316 A1 | 7/2008 | Eid et al. |
| 2008/0176769 A1 | 7/2008 | Rank et al. |
| 2008/0199874 A1 | 8/2008 | Otto et al. |
| 2008/0199932 A1 | 8/2008 | Hanzel et al. |
| 2008/0206764 A1 | 8/2008 | Williams et al. |
| 2008/0212960 A1 | 9/2008 | Lundquist et al. |
| 2008/0241951 A1 | 10/2008 | Battulga et al. |
| 2009/0026082 A1 | 1/2009 | Rothberg et al. |
| 2009/0035777 A1 | 2/2009 | Kokoris et al. |
| 2009/0099041 A1 | 4/2009 | Church et al. |
| 2009/0127589 A1 | 5/2009 | Rothberg et al. |
| 2010/0035253 A1 | 2/2010 | Gordon et al. |
| 2010/0092957 A1 | 4/2010 | Zhao et al. |
| 2010/0137143 A1 | 6/2010 | Rothberg et al. |
| 2010/0152050 A1 | 6/2010 | Gordon et al. |
| 2010/0159531 A1 | 6/2010 | Gordon et al. |
| 2010/0188073 A1 | 7/2010 | Rothberg et al. |
| 2010/0197507 A1 | 8/2010 | Rothberg et al. |
| 2010/0301398 A1 | 12/2010 | Rothberg et al. |
| 2010/0323350 A1 | 12/2010 | Gordon et al. |
| 2011/0028334 A1 | 2/2011 | Hayden |
| 2011/0172420 A1 | 7/2011 | Zilles et al. |
| 2011/0190486 A1 | 8/2011 | Zilles et al. |
| 2011/0223677 A1 | 9/2011 | Arden-Jacob et al. |

OTHER PUBLICATIONS

Lin X, Flint JA, Azaro M, Coradetti T, Kopacka WM, Streck DL, Wang Z, Dermody J, Mandecki W. Microtransponder-based multiplex assay for genotyping cystic fibrosis. Clin Chem. Jul. 2007; 53(7):1372-6. Epub May 17, 2007.*

Ju et al. Supplementary Information. Proc Natl Acad Sci U S A. Dec. 26, 2006; 103(52):19635-40. Epub Dec. 14, 2006.*

Xu H, Sha MY, Wong EY, Uphoff J, Xu Y, Treadway JA, Truong A, O'Brien E, Asquith S, Stubbins M, Spurr NK, Lai EH, Mahoney W. Multiplexed SNP genotyping using the Qbead system: a quantum dot-encoded microsphere-based assay. Nucleic Acids Res. Apr. 15, 2003; 31(8):e43. pp. 1-10.*

Haugland R.P., "The Handbook: A Guide to Fluorescent Probes and Labeling Technologies," in: Molecular Probes, 10th Edition, Spence M.T.Z., ed., Invitrogen Detection Technologies, United States of America, 2005, Table of Contents.

International Search Report and Written Opinion for Application No. PCT/US2013/065289, mailed on Jan. 17, 2014, 12 pages.

Ju J., et al., "Four-Color DNA Sequencing by Synthesis using Cleavable Fluorescent Nucleotide Reversible Terminators," Proceedings of the National Academy of Sciences, 2006, vol. 103 (52), pp. 19635-19640.

Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.

Maclean D., et al., "Application of 'next-generation' Sequencing Technologies to Microbial Genetics," Nature Reviews Microbiology, 2009, vol. 7 (4), pp. 287-296.

Margulies M., et al., "Genome Sequencing in Microfabricated High-Density Picolitre Reactors," Nature, 2005, vol. 437 (7057), pp. 376-380.

Moudrianakis E.N., et al., "Base Sequence Determination in Nucleic Acids with the Electron Microscope, III. Chemistry and Microscopy of Guanine-Labeled DNA," Proceedings of the National Academy of Sciences, 1965, vol. 53 (3), pp. 564-571.

Pennisi E., "Genomics. Semiconductors Inspire New Sequencing Technologies," Science, 2010, vol. 327 (5970), pp. 1190.

Soni G.V., et al., "Progress toward Ultrafast DNA Sequencing Using Solid-State Nanopres," Clinical Chemistry, 2007, vol. 53 (11), pp. 1996-2001.

Voelkerding K.V., et al., "Next-Generation Sequencing: from Basic Research to Diagnostics," Clinical Chemistry, 2009, vol. 55 (4), pp. 641-658.

\* cited by examiner

METHODS AND APPARATUS TO SEQUENCE A NUCLEIC ACID

FIELD OF THE DISCLOSURE

This disclosure relates generally to medical diagnostic equipment and, more particularly, to methods and apparatus to sequence a nucleic acid.

BACKGROUND

Nucleic acids are formed by chains of linked units called nucleotides. Nucleotides are molecules that are joined to create structural units of the nucleic acids ribonucleic acid (RNA) and deoxyribonucleic acid (DNA). A nucleotide includes a phosphate group, a sugar (ribose in the case of RNA and deoxyribose for DNA) and a nucleobase. The nucleobases are used in base pairing of strands of nucleotides to form higher-level structures such as the well-known double helix. The four bases found in DNA are adenine (A), cytosine (C), guanine (G) and thymine (T). In a DNA double helix, each type of nucleobase on one strand normally interacts with just one type of nucleobase on the other strand, which is known as complementary base pairing. Specifically, A only bonds to T and C only bonds to G. The RNA nucleobases include uracil (U) instead of thymine. Because of the importance of DNA and RNA, knowledge of a DNA or RNA sequence is useful for many purposes including, for example, to identify, diagnose and develop treatments for pathological, contagious or genetic diseases.

Nucleic acid sequencing chemistries include sequencing-by-synthesis (SBS) or sequencing-by-ligation (SBL) strategies. These strategies typically use random or ordered two-dimensional (2D) arrays for tracking sequence identity data. These array densities are extremely high, ranging from $10^5$ or $10^7$ features (or higher for single molecule detection). As the nucleotide chain grows from the action of the polymerase (SBS) or ligase (SBL), labels are incorporated and detected by readers. When a base or nucleic acid associated with a label is identified, the base is assigned a feature on the array by capturing a 2D optical image. However, the optical resolution needed to separate spectral data from these high densities arrays requires very long exposure times, resulting in average run times of hours to several days. In addition, the optical images acquired from successive sequencing cycles can easily reach the terabyte size, which creates a huge demand on algorithm computation time and data storage.

DETAILED DESCRIPTION

Figure 1:
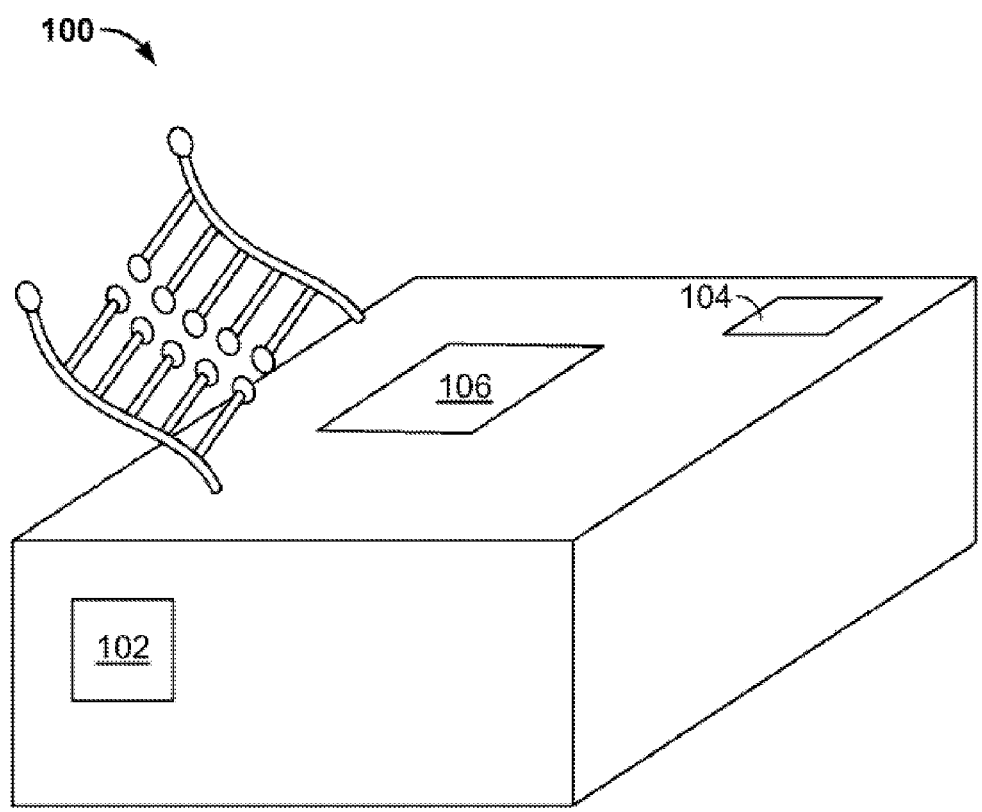
FIG. 1 is a schematic diagram of an example microtransponder.

This disclosure relates to methods and apparatus to sequence a nucleic acid as used, for example, in medical diagnostic equipment. The examples disclosed herein may be used to determine the nucleic acid sequence of an organism, a gene, and/or an amplified target using a combination of microtransponder technology and next-generation sequencing, including but not limited to sequencing-by-synthesis (SBS) or sequencing-by-ligation (SBL) chemistry. These examples may be used as general diagnostic systems and methods for detection of pathogenic organisms (bacterial and/or viral), RNA detection, DNA detection, whole genome de novo sequencing, gene expression, single-nucleotide polymorphism (SNP) and/or genetic testing where next-generation sequencing is used as a back end detection system. These examples may be used in many applications such as, for example, clinical diagnostics, hospital-acquired infections diagnosis, epidemiologic surveillance, forensics, research discovery and/or other suitable uses.

Sequencing may be by any method known in the art. In certain embodiments, sequencing is sequencing by synthesis. In other embodiments, sequencing is single molecule sequencing by synthesis. And, in some embodiments, sequencing is by sequencing by ligation (SBL). Other sequencing technologies that are encompassed by the technology are discussed throughout. Sequencing by synthesis can include the incorporation of dye labeled nucleotides, chain termination, ion/proton sequencing, pyrophosphate sequencing, or the like. Single molecule techniques can include staggered sequencing, where the sequencing reaction is paused to determine the identity of the incorporated nucleotide.

In certain embodiments, sequencing involves hybridizing a primer to a template (e.g., a nucleic acid to be sequenced) to form a template/primer duplex, contacting the duplex with a polymerase enzyme in the presence of detectably labeled nucleotides under conditions that permit the polymerase to add nucleotides to the primer in a template-dependent manner, detecting a signal from the incorporated labeled nucleotide, and sequentially repeating the contacting and detecting steps at least once, wherein sequential detection of incorporated labeled nucleotides determines the sequence of the nucleic acid. Exemplary detectable labels include radiolabels, metallic labels, quantum dots, fluorescent labels, luminescent labels, mass labels, enzymatic labels, etc. In particular embodiments, the detectable label may be an optically detectable label, such as a fluorescent label. Exemplary fluorescent labels (for sequencing and/or other purposes such as labeling a nucleic acid, primer, probe, etc.) include cyanine, rhodamine, fluorescein, coumarin, BODIPY, alexa, or conjugated multi-dyes.

In some embodiments, a target nucleic acid (e.g., a DNA and/or RNA) is immobilized. For example, in some embodiments a target nucleic acid is bound to another entity such as a capture probe, e.g., a complementary nucleic acid (e.g., that hybridizes to the target nucleic acid(s)), an antibody, or another capture technology (e.g., in some embodiments, the nucleic acid comprises a tag or other moiety that is recognized (e.g., bound) by a capture entity, e.g., in the case of a biotinylated nucleic acid bound to an immobilized avidin moiety).

A particular and exemplary SBS process involves segmenting a DNA sample and attaching a poly(A) tail at one end, which is washed over, for example, a glass cover slip coated in poly(T) molecules. A hybridizes with T and holds the DNA segment in place. Different DNA bases, which are joined to labels such as, for example, dye molecules, are washed over the fixed segments multiple times. Base pairs form to build the double helix. The labels indicate what bases are bound in pairs. An image is taken and the sequence is determined by reading the labels.

A particular and exemplary SBL process includes a target strand of an unknown DNA sequence that is flanked on at least one end by a known sequence. An anchor strand is introduced to bind to the known sequence. A mixed pool of labeled oligonucleotides (short nucleic acid polymers, typically with fifty or fewer bases) is introduced. The oligonucleotides hybridize to the target next to the anchor. DNA ligase joins the oligonucleotide to the anchor when the bases of the oligonucleotide match the unknown (target) DNA sequence. Based on the label (e.g., radiolabels, metallic labels, quantum dots, fluorescent labels, luminescent labels, mass labels, enzymatic labels), the unknown target nucleotide sequence can be identified.

The example systems and methods disclosed herein use microtransponders to selectively identify added nucleotides in a sequencing reaction. In some embodiments, the technology comprises use of an identification tool such as, for example, a flow reader, that identifies both a unique identification tag for each of a plurality of microtransponders and a label associated with a nucleotide base added to the nucleotide sequence. In some embodiments, the identification tool (e.g., an identification station and/or a flow meter) comprises a detector to detect the label associated with a nucleotide base. In some embodiments, the detector is a CCD, a CMOS, an ion sensor, such as an ion sensitive layer overlying a CMOS, a current detector, or the like. In some embodiments the detector is associated with an excitation system to cause a label, such as a fluorescent dye, to emit a signal. In some embodiments, the detector is associated with an illumination source, such as arc lamp, a laser, a light emitting diode (LED), or the like. In particular embodiments, the detector is associated with optics for the transmission of light from an illumination source to the sample or from the sample to the imaging or detection sensor. Alternatively, in some embodiments the detector is not associated with include an illumination source, such as for example, when a signal is produced spontaneously as a result of a sequencing reaction. For example, a signal can be produced by the interaction of a released moiety, such as a released ion interacting with an ion sensitive layer, or a pyrophosphate reacting with an enzyme or other catalyst to produce a chemiluminescent signal. In another example, a detector detects changes in an electrical current, voltage, or resistance without the need for an illumination source.

Accordingly, use of the technology according to embodiments described (e.g., comprising identifying both a unique identification tag for each of a plurality of microtransponders and a label associated with a nucleotide base added to the nucleotide sequence) changes the detection format from a two-dimensional (2D) array to a three-dimensional (3D) array, thereby eliminating the use of 2D Cartesian coordinates for sequence identification.

The example microtransponders are read with an identification device (e.g., comprising an identification tool) such as, for example, a flow meter (e.g., a flow reader comprising a detector, e.g., as described herein) and, therefore, there is no need to optically detect random or ordered high density arrays. After each round of synthesis or ligation, the microtransponders are passed through the flow reader where each transponder is identified and the label, e.g. fluorescence, is detected. A positive fluorescence indicates an added base; a negative fluorescence indicates no base was added. After each detection, the microtransponders may be re-suspended in a reagent for subsequent rounds of base addition and detection. There is no need for complex optical imaging hardware to resolve high density 2D array features. Thus, run times are significantly reduced. In addition, a digital "yes" or "no" detection signal from the microtransponders save significant storage space compared to traditional systems in which large data image files are stored during each run. Furthermore, high throughput is possible with the flow reader. An example flow reader can handle a transfer rate of, for example, about 1,000 microtransponders per second, which translates to approximately 3.5 million detect events per hour. An example memory or storage comprises a 64-bit ROM, which translates to more than $10^{17}$ different identifications, which is more than enough information to sequence the human genome.

An example system disclosed herein includes a microtransponder having a surface to which a nucleic acid target is to be captured via a capture probe. In some embodiments, systems include an amplification station to clonally amplify the nucleic acid target on the surface to form surface-bound clonal targets. In addition, the example system includes a reaction station to subject the surface-bound targets (e.g., in some embodiments, the amplified clonal targets) to a sequencing reaction (e.g., a first sequencing reaction) (e.g., a polymerization reaction (e.g., a first polymerization reaction), a ligation reaction (e.g., a first ligation reaction), etc.) to add a first nucleobase (e.g., a labeled nucleobase) or nucleotide base that is complementary to a nucleotide base (e.g., a first nucleotide base) in a sequence of the nucleic acid target. The example system also includes a wash station to remove an extraneous sequencing reaction reagent and/or byproduct (e.g., a polymerization reagent resulting from a polymerization reaction (e.g., the first polymerization reaction) or an extraneous ligation reagent resulting from a ligation reaction (e.g., the first ligation reaction)). Furthermore, the example system includes an identification station to determine an identity of a (e.g., each) nucleotide base (e.g., the first nucleotide base) in the sequence of the nucleic acid target and/or an identity of a nucleotide base (e.g., the first nucleotide base; e.g., a labeled nucleotide base) using a microtransponder identification number and, in some embodiments, a label (e.g., a first label) of a labeled nucleotide base (e.g., the first labeled nucleotide base), respectively.

The amplification station is to subject the surface-bound clonal targets to a second through an nth number of subsequent polymerization or ligation reaction(s) to sequentially add a second through nth labeled nucleotide base that are respectively complementary to a second through nth nucleotide base in the sequence of the nucleic acid target, wherein the nth number is based on the number of nucleotide bases in the sequence of the nucleic acid target. In addition, the wash station is to remove the extraneous polymerization or ligation reagent resulting from the second through nth polymerization or ligation reagents after the addition of each of the second through nth label nucleotide bases. Furthermore, the identification station is to determine, after the addition of each of the second through nth label nucleotide bases, an identity of each of the second through nth nucleotide bases in the sequence of the nucleic acid target and an identity of each of the second through nth labeled nucleotide bases using the microtransponder identification number and a second through nth label of the second through nth labeled nucleotide base, respectively.

In some examples, the capture probe may comprise DNA or RNA and the nucleic acid target may comprise DNA or RNA. Also, in some examples, the amplification station is to clonally amplify the nucleic acid target using emulsion polymerase chain reaction.

The technology is not limited in the nucleic acid sequencing technology. Various embodiments of nucleic acid sequencing platforms (e.g., a nucleic acid sequencer) include components as described below. According to various embodiments, a sequencing instrument includes a fluidic delivery and control unit, a sample processing unit, a signal detection unit, and a data acquisition, analysis and control unit. Various embodiments of the instrument provide for automated sequencing that is used to gather sequence information from a plurality of sequences in parallel and/or substantially simultaneously.

In some embodiments, the fluidics delivery and control unit includes a reagent delivery system. The reagent delivery system includes a reagent reservoir for the storage of various reagents. The reagents can include RNA-based primers, forward/reverse DNA primers, nucleotide mixtures for sequencing-by-synthesis, buffers, wash reagents, blocking reagents, stripping reagents, and the like. Additionally, the reagent delivery system can include a pipetting system or a continuous flow system that connects the sample processing unit with the reagent reservoir.

In some embodiments, a data acquisition analysis and control unit monitors various system parameters. The system parameters can include temperature of various portions of the instrument, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of the instruments and systems are used to practice sequencing methods such as sequencing by synthesis, single molecule methods, and other sequencing techniques. Sequencing by synthesis can include the incorporation of dye labeled nucleotides, chain termination, ion/proton sequencing, pyrophosphate sequencing, or the like. Single molecule techniques can include staggered sequencing, where the sequencing reactions are paused to determine the identity of the incorporated nucleotide.

In some embodiments, the sequencing instrument determines the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In some embodiments, the nucleic acid can include or be derived from a fragment library, a mate pair library, a ChIP fragment, or the like. In particular embodiments, the sequencing instrument can obtain the sequence information from a single nucleic acid molecule or from a group of substantially identical nucleic acid molecules.

In some embodiments, the sequencing instrument can output nucleic acid sequencing read data in a variety of different output data file types/formats, including, but not limited to: *.txt, *.fasta, *.csfasta, *seq.txt, *qseq.txt, *.fastq, *.sff, *prb.txt, *.sms, *srs, and/or *.qv.

In some embodiments, the technology comprises a next-generation sequencing technology. Particular sequencing technologies contemplated by the technology are next-generation sequencing (NGS) methods that share the common feature of massively parallel, high-throughput strategies, with the goal of lower costs in comparison to older sequencing methods (see, e.g., Voelkerding et al., Clinical Chem., 55: 641-658, 2009; MacLean et al., Nature Rev. Microbiol., 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., Clinical Chem., 55: 641-658, 2009; MacLean et al., Nature Rev. Microbiol., 7: 287-296; U.S. Pat. Nos. 6,210,891; 6,258,568; each herein incorporated by reference in its entirety), the NGS fragment library is clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and 106 sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Microbiol., 7: 287-296; U.S. Pat. Nos. 6,833,246; 7,115,400; 6,969,488; each herein incorporated by reference in its entirety), sequencing data are produced in the form of shorter-length reads. In this method, the fragments of the NGS fragment library are captured on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 100 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. Nos. 5,912,148; 6,130,073; each herein incorporated by reference in their entirety) also involves clonal amplification of the NGS fragment library by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, HeliScope by Helicos BioSciences is employed (Voelkerding et al., Clinical Chem., 55: 641-658, 2009; MacLean et al., Nature Rev. Microbiol., 7: 287-296; U.S. Pat. Nos. 7,169,560; 7,282,337; 7,482,120; 7,501,245; 6,818,395; 6,911,345; 7,501,245; each herein incorporated by reference in their entirety). Sequencing is achieved by addition of polymerase and serial addition of fluorescently-labeled dNTP reagents. Incorporation events result in a fluor signal corresponding to the dNTP, and signal is captured by a CCD camera before each round of dNTP addition. Sequence read length ranges from 25-50 nucleotides, with overall output exceeding 1 billion nucleotide pairs per analytical run.

In some embodiments, 454 sequencing by Roche is used (Margulies et al. (2005) Nature 437: 376-380). 454 sequencing involves two steps. In the first step, DNA is sheared into fragments of approximately 300-800 base pairs and the fragments are blunt ended. Oligonucleotide adaptors are then ligated to the ends of the fragments. The adaptors serve as primers for amplification and sequencing of the fragments. The fragments can be attached to DNA capture beads, e.g., streptavidin-coated beads using, e.g., an adaptor that contains a 5'-biotin tag. The fragments attached to the beads are PCR amplified within droplets of an oil-water emulsion. The result is multiple copies of clonally amplified DNA fragments on each bead. In the second step, the beads are captured in wells (pico-liter sized). Pyrosequencing is performed on each DNA fragment in parallel. Addition of one or more nucleotides generates a light signal that is recorded by a CCD camera in a sequencing instrument. The signal strength is proportional to the number of nucleotides incorporated. Pyrosequencing makes use of pyrophosphate (PPi) which is released upon nucleotide addition. PPi is converted to ATP by ATP sulfurylase in the presence of adenosine 5' phosphosulfate. Luciferase uses ATP to convert luciferin to oxyluciferin, and this reaction generates light that is detected and analyzed.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a fragment of the NGS fragment library to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs. However, the cost of acquiring a pH-mediated sequencer is approximately $50,000, excluding sample preparation equipment and a server for data analysis.

Another exemplary nucleic acid sequencing approach that may be adapted for use with the present invention was developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "HIGH THROUGHPUT NUCLEIC ACID SEQUENCING BY EXPANSION," filed Jun. 19, 2008, which is incorporated herein in its entirety.

Other single molecule sequencing methods include real-time sequencing by synthesis using a VisiGen platform (Voelkerding et al., Clinical Chem., 55: 641-58, 2009; U.S. Pat. No. 7,329,492; U.S. patent application Ser. Nos. 11/671, 956; 11/781,166; each herein incorporated by reference in their entirety) in which fragments of the NGS fragment library are immobilized, primed, then subjected to strand extension using a fluorescently-modified polymerase and florescent acceptor molecules, resulting in detectable fluorescence resonance energy transfer (FRET) upon nucleotide addition.

Another real-time single molecule sequencing system developed by Pacific Biosciences (Voelkerding et al., Clinical Chem., 55: 641-658, 2009; MacLean et al., Nature Rev. Microbiol., 7: 287-296; U.S. Pat. Nos. 7,170,050; 7,302,146; 7,313,308; 7,476,503; all of which are herein incorporated by reference) utilizes reaction wells 50-100 nm in diameter and encompassing a reaction volume of approximately 20 zepto-liters (10-21 l). Sequencing reactions are performed using immobilized template, modified phi29 DNA polymerase, and high local concentrations of fluorescently labeled dNTPs. High local concentrations and continuous reaction conditions allow incorporation events to be captured in real time by fluor signal detection using laser excitation, an optical waveguide, and a CCD camera.

In certain embodiments, the single molecule real time (SMRT) DNA sequencing methods using zero-mode waveguides (ZMWs) developed by Pacific Biosciences, or similar methods, are employed. With this technology, DNA sequencing is performed on SMRT chips, each containing thousands of zero-mode waveguides (ZMWs). A ZMW is a hole, tens of nanometers in diameter, fabricated in a 100 nm metal film deposited on a silicon dioxide substrate. Each ZMW becomes a nanophotonic visualization chamber providing a detection volume of just 20 zeptoliters (10 L). At this volume, the activity of a single molecule can be detected amongst a background of thousands of labeled nucleotides. The ZMW provides a window for watching DNA polymerase as it performs sequencing by synthesis. Within each chamber, a single DNA polymerase molecule is attached to the bottom surface such that it permanently resides within the detection volume. Phospholinked nucleotides, each type labeled with a different colored fluorophore, are then introduced into the reaction solution at high concentrations which promote enzyme speed, accuracy, and processivity. Due to the small size of the ZMW, even at these high, biologically relevant concentrations, the detection volume is occupied by nucleotides only a small fraction of the time. In addition, visits to the detection volume are fast, lasting only a few microseconds, due to the very small distance that diffusion has to carry the nucleotides. The result is a very low background.

In some embodiments, nanopore sequencing is used (Soni G V and Meller A. (2007) Clin Chem 53: 1996-2001). A nanopore is a small hole, of the order of 1 nanometer in diameter. Immersion of a nanopore in a conducting fluid and application of a potential across it results in a slight electrical current due to conduction of ions through the nanopore. The amount of current which flows is sensitive to the size of the nanopore. As a DNA molecule passes through a nanopore, each nucleotide on the DNA molecule obstructs the nanopore to a different degree. Thus, the change in the current passing through the nanopore as the DNA molecule passes through the nanopore represents a reading of the DNA sequence.

In some embodiments, a sequencing technique uses a chemical-sensitive field effect transistor (chemFET) array to sequence DNA (for example, as described in US Patent Application Publication No. 20090026082). In one example of the technique, DNA molecules are placed into reaction chambers, and the template molecules are hybridized to a sequencing primer bound to a polymerase. Incorporation of one or more triphosphates into a new nucleic acid strand at the 3' end of the sequencing primer can be detected by a change in current by a chemFET. An array can have multiple chemFET sensors. In another example, single nucleic acids can be attached to beads, and the nucleic acids can be amplified on the bead, and the individual beads can be transferred to individual reaction chambers on a chemFET array, with each chamber having a chemFET sensor, and the nucleic acids can be sequenced.

In some embodiments, sequencing technique uses an electron microscope (Moudrianakis E. N. and Beer M. Proc Natl Acad Sci USA. 1965 March; 53:564-71). In one example of the technique, individual DNA molecules are labeled using metallic labels that are distinguishable using an electron microscope. These molecules are then stretched on a flat surface and imaged using an electron microscope to measure sequences.

In some embodiments, "four-color sequencing by synthesis using cleavable fluorescents nucleotide reversible terminators" as described in Turro, et al. PNAS 103: 19635-40 (2006) is used, e.g., as commercialized by Intelligent BioSystems. The technology described in U.S. Pat. Appl. Pub. Nos. 2010/0323350, 2010/0063743, 2010/0159531, 20100035253, 20100152050, incorporated herein by reference for all purposes.

Processes and systems for such real time sequencing that may be adapted for use with the invention are described in, for example, U.S. Pat. No. 7,405,281, entitled "Fluorescent nucleotide analogs and uses therefor", issued Jul. 29, 2008 to Xu et al.; U.S. Pat. No. 7,315,019, entitled "Arrays of optical confinements and uses thereof", issued Jan. 1, 2008 to Turner et al.; U.S. Pat. No. 7,313,308, entitled "Optical analysis of molecules", issued Dec. 25, 2007 to Turner et al.; U.S. Pat. No. 7,302,146, entitled "Apparatus and method for analysis of molecules", issued Nov. 27, 2007 to Turner et al.; and U.S. Pat. No. 7,170,050, entitled "Apparatus and methods for optical analysis of molecules", issued Jan. 30, 2007 to Turner et al.; and U.S. Pat. Pub. Nos. 20080212960, entitled "Methods and systems for simultaneous real-time monitoring of optical signals from multiple sources", filed Oct. 26, 2007 by Lundquist et al.; 20080206764, entitled "Flow-cell system for single molecule detection", filed Oct. 26, 2007 by Williams et al.; 20080199932, entitled "Active surface coupled polymerases", filed Oct. 26, 2007 by Hanzel et al.; 20080199874, entitled "CONTROLLABLE STRAND SCISSION OF MINI CIRCLE DNA", filed Feb. 11, 2008 by Otto et al.; 20080176769, entitled "Articles having localized molecules disposed thereon and methods of producing same", filed Oct. 26, 2007 by Rank et al.; 20080176316, entitled "Mitigation of photodamage in analytical reactions", filed Oct. 31, 2007 by Eid et al.; 20080176241, entitled "Mitigation of photodamage in analytical reactions", filed Oct. 31, 2007 by Eid et al.; 20080165346, entitled "Methods and systems for simultaneous real-time monitoring of optical signals from multiple sources", filed Oct. 26, 2007 by Lundquist et al.; 20080160531, entitled "Uniform surfaces for hybrid material substrates and methods for making and using same", filed Oct. 31, 2007 by Korlach; 20080157005, entitled "Methods and systems for simultaneous real-time monitoring of optical signals from multiple sources", filed Oct. 26, 2007 by Lundquist et al.; 20080153100, entitled "Articles having localized molecules disposed thereon and methods of producing same", filed Oct. 31, 2007 by Rank et al.; 20080153095, entitled "CHARGE SWITCH NUCLEOTIDES", filed Oct. 26, 2007 by Williams et al.; 20080152281, entitled "Substrates, systems and methods for analyzing materials", filed Oct. 31, 2007 by Lundquist et al.; 20080152280, entitled "Substrates, systems and methods for analyzing materials", filed Oct. 31, 2007 by Lundquist et al.; 20080145278, entitled "Uniform surfaces for hybrid material substrates and methods for making and using same", filed Oct. 31, 2007 by Korlach; 20080128627, entitled "SUBSTRATES, SYSTEMS AND METHODS FOR ANALYZING MATERIALS", filed Aug. 31, 2007 by Lundquist et al.; 20080108082, entitled "Polymerase enzymes and reagents for enhanced nucleic acid sequencing", filed Oct. 22, 2007 by Rank et al.; 20080095488, entitled "SUBSTRATES FOR PERFORMING ANALYTICAL REACTIONS", filed Jun. 11, 2007 by Foquet et al.; 20080080059, entitled "MODULAR OPTICAL COMPONENTS AND SYSTEMS INCORPORATING SAME", filed Sep. 27, 2007 by Dixon et al.; 20080050747, entitled "Articles having localized molecules disposed thereon and methods of producing and using same", filed Aug. 14, 2007 by Korlach et al.; 20080032301, entitled "Articles having localized molecules disposed thereon and methods of producing same", filed Mar. 29, 2007 by Rank et al.; 20080030628, entitled "Methods and systems for simultaneous real-time monitoring of optical signals from multiple sources", filed Feb. 9, 2007 by Lundquist et al.; 20080009007, entitled "CONTROLLED INITIATION OF PRIMER EXTENSION", filed Jun. 15, 2007 by Lyle et al.; 20070238679, entitled "Articles having localized molecules disposed thereon and methods of producing same", filed Mar. 30, 2006 by Rank et al.; 20070231804, entitled "Methods, systems and compositions for monitoring enzyme activity and applications thereof", filed Mar. 31, 2006 by Korlach et al.; 20070206187, entitled "Methods and systems for simultaneous real-time monitoring of optical signals from multiple sources", filed Feb. 9, 2007 by Lundquist et al.; 20070196846, entitled "Polymerases for nucleotide analog incorporation", filed Dec. 21, 2006 by Hanzel et al.; 20070188750, entitled "Methods and systems for simultaneous real-time monitoring of optical signals from multiple sources", filed Jul. 7, 2006 by Lundquist et al.; 20070161017, entitled "MITIGATION OF PHOTODAMAGE IN ANALYTICAL REACTIONS", filed Dec. 1, 2006 by Eid et al.; 20070141598, entitled "Nucleotide Compositions and Uses Thereof", filed Nov. 3, 2006 by Turner et al.; 20070134128, entitled "Uniform surfaces for hybrid material substrate and methods for making and using same", filed Nov. 27, 2006 by Korlach; 20070128133, entitled "Mitigation of photodamage in analytical reactions", filed Dec. 2, 2005 by Eid et al.; 20070077564, entitled "Reactive surfaces, substrates and methods of producing same", filed Sep. 30, 2005 by Roitman et al.; 20070072196, entitled "Fluorescent nucleotide analogs and uses therefore", filed Sep. 29, 2005 by Xu et al; and 20070036511, entitled "Methods and systems for monitoring multiple optical signals from a single source", filed Aug. 11, 2005 by Lundquist et al.; and Korlach et al. (2008) "Selective aluminum passivation for targeted immobilization of single DNA polymerase molecules in zero-mode waveguide nanostructures" PNAS 105(4): 1176-81, all of which are herein incorporated by reference in their entireties.

In some examples, at least one of the labeled nucleotide bases comprises a set of labeled nucleotide bases. The term "label" or "tag" are used interchangeably herein to refer to any chemical moiety attached to a nucleotide or nucleic acid, wherein the attachment may be covalent or non-covalent. Preferably, the label is detectable and renders the nucleotide or nucleic acid detectable to the practitioner of the technology. Exemplary detectable labels that find use with the technology provided herein include, for example, a fluorescent label, a chemiluminescent label, a quencher, a radioactive label, biotin, and gold, or combinations thereof. Detectable labels include luminescent molecules, fluorochromes, fluorescent quenching agents, colored molecules (e.g., chromogens used for in situ hybridization (ISH, FISH) and bright field imaging applications), radioisotopes, or scintillants. Detectable labels also include any useful linker molecule (such as biotin, avidin, digoxigenin, streptavidin, HRP, protein A, protein G, antibodies or fragments thereof, Grb2, polyhistidine, $Ni^{2+}$, FLAG tags, myc tags), heavy metals, enzymes (examples include alkaline phosphatase, peroxidase, and luciferase), electron donors/acceptors, acridinium esters, dyes, and calorimetric substrates. It is also envisioned that a change in mass may be considered a detectable label, e.g., as finds use in surface plasmon resonance detection.

In some embodiments, the label comprises a fluorescently detectable moiety that is based on a dye, wherein the dye is a xanthene, fluorescein, rhodamine, BODIPY, cyanine, coumarin, pyrene, phthalocyanine, phycobiliprotein, ALEXA FLUOR® 350, ALEXA FLUOR® 405, ALEXA FLUOR® 430, ALEXA FLUOR® 488, ALEXA FLUOR® 514, ALEXA FLUOR® 532, ALEXA FLUOR® 546, ALEXA FLUOR® 555, ALEXA FLUOR® 568, ALEXA FLUOR® 568, ALEXA FLUOR® 594, ALEXA FLUOR® 610, ALEXA FLUOR® 633, ALEXA FLUOR® 647, ALEXA FLUOR® 660, ALEXA FLUOR® 680, ALEXA FLUOR® 700, ALEXA FLUOR® 750, a fluorescent semiconductor crystal, or a squaraine dye. In some embodiments, the tag or label comprises a radioisotope, a spin label, a quantum dot, or a bioluminescent moiety. In some embodiments, the label is a fluorescently detectable moiety as described in, e.g., Haugland (September 2005) MOLECULAR PROBES HANDBOOK OF FLUORESCENT PROBES AND RESEARCH CHEMICALS (10th ed.), which is herein incorporated by reference in its entirety.

In some embodiments the label (e.g., a fluorescently detectable label) is one available from ATTO-TEC GmbH (Am Eichenhang 50, 57076 Siegen, Germany), e.g., as described in U.S. Pat. Appl. Pub. Nos. 20110223677, 20110190486, 20110172420, 20060179585, and 20030003486; and in U.S. Pat. No. 7,935,822, all of which are incorporated herein by reference.

In some embodiments, at least one of the labeled nucleotide bases comprises one or more of a radiolabel, metallic label, quantum dot, fluorescent label, luminescent label, mass labels, enzymatic label, etc. In particular embodiments, the detectable label may be an optically detectable label, such as a fluorescent label. Exemplary fluorescent labels (for sequencing and/or other purposes such as labeling a nucleic acid, primer, probe, etc.) include cyanine, rhodamine, fluorescein, coumarin, BODIPY, alexa, or conjugated multi-dyes. In some examples, at least one of the labeled nucleotide bases may comprise an optical label and/or at least one of the labeled nucleotide bases may comprise an electrochemical label.

In some example systems, the identification station comprises a flow meter. In some examples, the reaction station is to use a single label for a plurality of nucleotide bases. In some examples, the reaction station is to use a different label for each nucleotide base to differentiate different nucleotide bases. In some examples, the reaction station is to add at least one of the first, second or nth labeled nucleotide base as a single base. In some examples, the reaction station is to add at least one of the first, second or nth labeled nucleotide bases as an oligonucleotide. In some examples, the oligonucleotide comprises up to about thirty nucleotides.

Some example systems disclosed herein include a plurality of microtransponders for a multiplex assay containing more than one nucleic acid target.

Also, some example systems disclosed herein include a microfluidic chip device comprising one or more of the amplification station, the reaction station, the wash station or the identification station.

In some examples, the nth number represents an end of substantially an entire sequence.

An example method disclosed herein includes subjecting a sequence of target nucleotide bases captured on a microtransponder to a plurality of sequencing reactions to build a sequence of labeled nucleotide bases that are complementary to and bound to the sequence of target nucleotide bases. The example method also includes identifying each labeled nucleotide base of the sequence of labeled nucleotide bases and each respective complementary target nucleotide base of the sequence of target nucleotide bases to which the labeled nucleotide base is bound after each sequencing reaction and prior to a subsequent sequencing reaction. In addition, the example method includes associating each labeled nucleotide base of the sequence of labeled nucleotide bases and each respective complementary target nucleotide base of the sequence of target nucleotide bases to which the labeled nucleotide base is bound with an identification number of the microtransponder.

Some examples also include clonally amplifying the target nucleotide bases via an emulsion polymerase chain reaction prior to sequencing reaction. In some examples, identifying the labeled nucleotide base comprises detecting the labeled nucleotide base with a flow meter.

Also, some example methods disclosed herein include using a single label for a plurality of nucleotide bases. Some example methods include using a different label for each nucleotide base to differentiate different nucleotide bases. Also, some example methods include adding the labeled nucleotide base as a single base. In addition, some example methods disclosed herein include adding the nth labeled nucleotide base as an oligonucleotide. Some example methods include using a plurality of microtransponders for a multiplex assay containing more than one nucleic acid target. Also, some example methods include performing at least a portion of the method in a microfluidic chip device. Furthermore, in some examples, the sequencing reactions repeat until substantially an entirety of the sequence of target nucleotide bases is identified.

Another example method disclosed herein includes capturing a nucleic acid target on a surface of a microtransponder via a capture probe, clonally amplifying the nucleic acid target on the surface to form surface-bound clonal targets and subjecting the surface-bound clonal targets to a first polymerization reaction or a first ligation reaction to add a first labeled nucleotide base that is complementary to a first nucleotide base in a sequence of the nucleic acid target. The example method also includes removing an extraneous polymerization reagent resulting from the first polymerization reaction or an extraneous ligation reagent resulting from the first ligation reaction and determining an identity of the first nucleotide base in the sequence of the nucleic acid target and an identity of the first labeled nucleotide base using a microtransponder identification number and a first label of the first labeled nucleotide base, respectively. Furthermore, the example method includes subjecting the surface-bound clonal targets to a second through an nth number of subsequent polymerization or ligation reactions to sequentially add a second through nth labeled nucleotide base that are respectively complementary to a second through nth nucleotide base in the sequence of the nucleic acid target. The nth number is based on the number of nucleotide bases in the sequence of the nucleic acid target. In addition, the example method includes removing the extraneous polymerization or ligation reagent resulting from the second through nth polymerization or ligation reagents after the addition of each of the second through nth label nucleotide bases and determining, after the addition of each of the second through nth label nucleotide bases, an identity of each of the second through nth nucleotide bases in the sequence of the nucleic acid target and an identity of each of the second through nth labeled nucleotide bases using the microtransponder identification number and a second through nth label of the second through nth labeled nucleotide base, respectively.

In some embodiments, the technology provided herein relates to a method (e.g., a method for sequencing a nucleic acid), the method comprising subjecting a sequence of target nucleotide bases captured on a microtransponder to a plurality of sequencing reactions to add a sequence of nucleotide bases that are complementary to and bound to the sequence of target nucleotide bases; identifying each added nucleotide base after each sequencing reaction; and associating each added nucleotide base of the sequence with an identification number of the microtransponder. In some embodiments, the target nucleotide bases are captured via a capture probe. In some embodiments, the target nucleotide bases comprise DNA or RNA. In some embodiments, the methods further comprise clonally amplifying the target nucleotide bases (e.g., an emulsion polymerase chain reaction, e.g., prior to the sequencing reaction). In some embodiments at least one of the added nucleotide bases comprises a label. The technology is not limited in the types of labels used, e.g., in some embodiments at least one of the added nucleotide bases comprises an optical label and in some embodiments at least one of the added nucleotide bases comprises an electrochemical label.

In some embodiments, identifying the added nucleotide base comprises detecting the added nucleotide base by employing a flow meter. In some embodiments, identifying comprises moving said added base from a reaction station of an apparatus to an identification station of said apparatus using said flow meter. In some embodiments, the identification station comprises a detector for detecting said added base, wherein said detector detects one or more of an optical signal, an electrical signal, and a chemical signal. The technology is not limited in the type of detector and/or detection mode, e.g., used to detect a label or a nucleotide. For instance, in some embodiments an added base is detected by a change in fluorescence, luminescence, pH, heat, hydrogen ion concentration, pyrophosphate concentration, or radioactivity. Moreover, in some embodiments a single label is used for a plurality of added nucleotide bases and in some embodiments a plurality of different labels is used for each added nucleotide base to differentiate different added nucleotide bases. And, in some embodiments the added base is added as a single base and in some embodiments the added base is added as an oligonucleotide (e.g., an oligonucleotide comprising up to about thirty nucleotides, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides).

In further embodiments, the methods comprise using a plurality of microtransponders for a multiplex assay containing more than one nucleic acid target. And, some embodiments provide a method comprising performing at least a portion of the method in a microfluidic chip device. The method finds use in sequencing a nucleic acid; thus in some embodiments the sequencing reactions repeat until substantially an entirety of the sequence of target nucleotide bases is identified.

Additional embodiments provide an apparatus comprising a microtransponder having a surface to which a nucleic acid target is to be captured via a capture probe; a reaction station to subject the surface-bound nucleic acid target to a plurality of sequencing reactions to add a sequence of nucleotide bases that are complementary to and bound to the sequence of target nucleotide bases; a wash station to remove an extraneous sequencing reagent resulting from the plurality of sequencing reactions; and an identification station to identify each added nucleotide base after each sequencing reaction. In some embodiments, the apparatus further comprises an amplification station to clonally amplify the nucleic acid target on the surface to form surface-bound clonal targets (e.g., in some embodiments, the amplification station is to subject the surface-bound nucleic acid target to a second through an nth number of subsequent sequencing reactions). In some embodiments, the second through the nth number of subsequent sequencing reactions add a second through an nth nucleotide base that are complementary to a second through an nth nucleotide base in the sequence of the nucleic acid target, wherein n is equal to or less than the number of nucleotide bases in the sequence of the nucleic acid target.

In embodiments comprising a wash station, some embodiments provide that the wash station is to remove the extraneous sequencing reagent resulting from the second through the nth sequencing reactions after the addition of each of the second through the nth nucleotide bases. Furthermore, in some embodiments the identification station is to determine an identity of each of the second through the nth nucleotide bases in the sequence of the nucleic acid target. And, moreover, embodiments are provided wherein the identification station associates each added nucleotide base of the sequence with an identification number of the microtransponder.

In some embodiments, a nucleotide base comprises a label. The apparatus is not limited in the type of label used for detection, e.g., in some embodiments a nucleotide base comprises an optical label and in some embodiments a nucleotide base comprises an electrochemical label. In some embodiments, the reaction station is to use a single label for a plurality of nucleotide bases. In some embodiments the reaction station is to use a different label for each nucleotide to differentiate different nucleotide bases In some embodiments, the capture probe comprises DNA or RNA. In some embodiments, the nucleic acid target comprises DNA or RNA.

In some embodiments, the amplification station is to clonally amplify the nucleic acid target using emulsion polymerase chain reaction. In some embodiments the identification station comprises a flow meter. In some embodiments, the identification station comprises a detector for detecting each added nucleotide base.

The apparatus is not limited in the type of signal detected. For example, in some embodiments a detector detects one or more of an optical signal, an electrical signal, and a chemical signal. In some embodiments the detector detects said added base by a change in fluorescence, luminescence, pH, heat, hydrogen ion concentration, pyrophosphate concentration, or radioactivity.

In some embodiments the identification station moves said added base from the reaction station of the apparatus to the identification station of said apparatus using said flow meter.

In some embodiments, each added nucleotide base is added as a single base and in some embodiments each added nucleotide base is added as a as an oligonucleotide (e.g., an oligonucleotide comprising up to about thirty nucleotides, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides).

Further embodiments provide an apparatus comprising a plurality of microtransponders for a multiplex assay containing more than one nucleic acid target. In addition, some embodiments provide an apparatus comprising a microfluidic chip device, e.g., a microfluidic chip device comprising one or more of the reaction station, the wash station, or the identification station, and/or, in some embodiments, the amplification station.

The apparatus finds use in providing a nucleotide sequence; thus, in some embodiments the nth number represents an end of substantially an entire sequence.

Additional method embodiments provide a method comprising subjecting a sequence of target nucleotide bases captured on a microtransponder to a plurality of sequencing reactions to add a sequence of nucleotide bases that are complementary to and bound to the sequence of target nucleotide bases; moving each added nucleotide base from a reaction station of an apparatus to an identification station of said apparatus using a flow meter; and identifying each added nucleotide base after each sequencing reaction. In some embodiments methods further comprise capturing a nucleic acid target on the surface of the microtransponder, e.g., in some embodiments the nucleic acid target is captured by a capture probe. In still further embodiments, the technology provides a method comprising amplifying the nucleic acid target to form surface-bound clonal targets. In some embodiments, methods further comprise clonally amplifying the target nucleotide bases, e.g., in some embodiments that provide a method wherein the clonally amplifying comprises an emulsion polymerase chain reaction (e.g., prior to the sequencing reaction).

In some embodiments the methods comprise removing an extraneous sequencing reagent. And, in some embodiments methods comprise repeating the sequencing reactions until substantially an entirety of the sequence of target nucleotide bases is identified.

In some embodiments, the target nucleotide bases comprise DNA or RNA.

The technology comprises use, in some embodiments, of a nucleotide comprising a label. For example, in some embodiments at least one of the added nucleotide bases comprises a label. The technology is not limited in the particular labels that are used, e.g., in some embodiments at least one of the added nucleotide bases comprises an optical label and, e.g., in some embodiments at least one of the added nucleotide bases comprises an electrochemical label. In some embodiments a single label is used for a plurality of added nucleotide bases and in some embodiments a plurality of different labels is used for each added nucleotide base to differentiate different added nucleotide bases. In some embodiments, the added base is added as a single base and in some embodiments the added base is added as an oligonucleotide (e.g., an oligonucleotide comprising up to about thirty nucleotides, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides).

In some embodiments, identifying the added nucleotide base comprises detecting the added nucleotide base by employing a flow meter. In some embodiments the identification station comprises a detector for detecting said added base, wherein said detector detects one or more of an optical signal, an electrical signal, and a chemical signal. In some embodiments the added base is detected by a change in fluorescence, luminescence, pH, heat, hydrogen ion concentration, pyrophosphate concentration, or radioactivity.

In some embodiments of the methods, methods comprise using a plurality of microtransponders for a multiplex assay containing more than one nucleic acid target. Some embodiments comprise performing at least a portion of the method in a microfluidic chip device, e.g., a microfluidic chip device comprising one or more of the reaction station, amplification station, washing station, and/or the identification station.

In some embodiments, the technology provided herein relates to a method (e.g., a method for sequencing a nucleic acid, the method comprising (e.g., comprising performing one or more of the following steps in any order on a microfluidic chip device) subjecting a sequence of target nucleotide bases (e.g., DNA and/or RNA) captured (e.g., by a capture probe) on a microtransponder (e.g., a plurality of microtransponders, e.g., used for a multiplex assay containing more than one nucleic acid target) to a plurality of sequencing reactions to add a sequence of nucleotide bases (e.g., comprising a label (e.g., an optical label, an electrochemical label, a mass label, etc.), e.g., a single label used for a plurality of added nucleotide bases and/or a plurality of different labels used for each added nucleotide base to differentiate different added nucleotide bases) that are complementary to and bound to the sequence of target nucleotide bases (e.g., adding the bases as a single base and/or as an oligonucleotide (e.g., an oligonucleotide comprising up to about thirty nucleotides, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides)); identifying each added nucleotide base after each sequencing reaction (e.g., detecting the added nucleotide base by employing a flow meter, e.g., moving said added base from a reaction station of an apparatus to an identification station (e.g., comprising a detector for detecting said added base, wherein said detector detects one or more of an optical signal, an electrical signal, and a chemical signal, e.g., detecting the added base by a change in fluorescence, luminescence, pH, heat, hydrogen ion concentration, pyrophosphate concentration, or radioactivity) of said apparatus using said flow meter); associating each added nucleotide base of the sequence with an identification number of the microtransponder; clonally amplifying the target nucleotide bases (e.g., an emulsion polymerase chain reaction, e.g., prior to the sequencing reaction); and/or repeating one or more steps until substantially an entirety of the sequence of target nucleotide bases is identified.

Additional embodiments provide an apparatus (e.g., comprising a microfluidic chip device, e.g., a microfluidic chip device comprising one or more of the following described reaction station, wash station, identification station, and/or amplification station) comprising a microtransponder (e.g., a plurality of microtransponders for a multiplex assay containing more than one nucleic acid target) having a surface to which a nucleic acid target (e.g., DNA and/or RNA) is to be captured via a capture probe (e.g., comprising DNA and/or RNA); a reaction station to subject the surface-bound nucleic acid target to a plurality of sequencing reactions to add a sequence of nucleotide bases (e.g., comprising a label (e.g., an optical label, an electrochemical label, a mass label); e.g., a single label used for a plurality of nucleotide bases and/or a different label used for each nucleotide to differentiate different nucleotide bases)) that are complementary to and bound to the sequence of target nucleotide bases (e.g., added as a single base and/or as an oligonucleotide (e.g., an oligonucleotide comprising up to about thirty nucleotides, e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides)); a wash station to remove an extraneous sequencing reagent resulting from the plurality of sequencing reactions (e.g., to remove the extraneous sequencing reagent resulting from the second through the nth sequencing reactions after the addition of each of the second through the nth nucleotide bases); and an identification station (e.g., comprising a flow meter and/or a detector for detecting each added nucleotide base (e.g., by an optical signal, an electrical signal, and/or a chemical signal; and/or by a change in fluorescence, luminescence, pH, heat, hydrogen ion concentration, pyrophosphate concentration, or radioactivity)) to identify each added nucleotide base after each sequencing reaction (e.g., to determine an identity of each of the second through the nth nucleotide bases in the sequence of the nucleic acid target; e.g., to associate each added nucleotide base of the sequence with an identification number of the microtransponder) and/or to move said added base from the reaction station of the apparatus to the identification station of said apparatus using the flow meter; an amplification station to clonally amplify the nucleic acid target on the surface to form surface-bound clonal targets (e.g., to clonally amplify the nucleic acid target using emulsion polymerase chain reaction; e.g., to subject the surface-bound nucleic acid target to a second through an nth number of subsequent sequencing reactions, e.g., to add a second through an nth nucleotide base that are complementary to a second through an nth nucleotide base in the sequence of the nucleic acid target, wherein n is equal to or less than the number of nucleotide bases in the sequence of the nucleic acid target and the nth number represents an end of substantially an entire sequence).

Example tangible machine readable storage medium having instructions, which when executed cause a machine to perform, for example, the disclosed example methods are disclosed herein. Example instructions cause a machine to capture a nucleic acid target on a surface of a microtransponder via a capture probe, clonally amplify the nucleic acid target on the surface to form surface-bound clonal targets and subject the surface-bound clonal targets to a first polymerization reaction or a first ligation reaction to add a first labeled nucleotide base that is complementary to a first nucleotide base in a sequence of the nucleic acid target. The example instructions also cause the machine to remove an extraneous polymerization reagent resulting from the first polymerization reaction or an extraneous ligation reagent resulting from the first ligation reaction and determine an identity of the first nucleotide base in the sequence of the nucleic acid target and an identity of the first labeled nucleotide base using a microtransponder identification number and a first label of the first labeled nucleotide base, respectively. Furthermore, the example instructions cause the machine to subject the surface-bound clonal targets to a second through an nth number of subsequent polymerization or ligation reactions to sequentially add a second through nth labeled nucleotide base that are respectively complementary to a second through nth nucleotide base in the sequence of the nucleic acid target. The nth number is based on the number of nucleotide bases in the sequence of the nucleic acid target. In addition, the example instructions cause a machine to remove the extraneous polymerization or ligation reagent resulting from the second through nth polymerization or ligation reagents after the addition of each of the second through nth label nucleotide bases and determining, after the addition of each of the second through nth label nucleotide bases, an identity of each of the second through nth nucleotide bases in the sequence of the nucleic acid target and an identity of each of the second through nth labeled nucleotide bases using the microtransponder identification number and a second through nth label of the second through nth labeled nucleotide base, respectively.

Turning now to the figures, FIG. 1 shows an example microtransponder 100 for use with the systems and methods disclosed herein. The example microtransponder 100 is a small chip-based device comprising, for example, silicon. In some examples, the microtransponder 100 has the dimensions 250 µm×250 µm×100 gm. The example microtransponder 100 includes a unique numerical identification number or tag 102, which may be, in some examples, a radio frequency identification (RFID) tag. The example microtransponder 100 includes an antenna 104 such as, for example, a loop antenna. The antenna 104 allows the microtransponder 100 to transmit the identification of the microtransponder stored on or associated with the identification tag 102 to an identification device (or reader) to identify the microtransponder 100. In some examples, the identification of the microtransponder is unique alphanumeric code or number. The microtransponder 100 also includes a photocell 106 that detects resident fluorescence of any labeled nucleotide base bound to the microtransponder 100, which is converted and transmitted as a digital "yes" or "no" signal as disclosed in more detail below.

The example microtransponder 100 has a surface that is derivatized with surface chemistry to carry capture probes. The capture probes are capable of hybridizing with specific nucleic acid sequences and are used to capture nucleic acid targets that are to be identified. In some examples, the capture probe comprises DNA or RNA.

A sample such as, for example, a blood or other bodily fluid sample containing unknown nucleic acid and/or potentially one or more nucleic acid targets is washed over or otherwise introduced to the surface of the microtransponder 100. In some examples, the nucleic acid target comprises DNA or RNA. In some examples, as shown in the example system 200 of FIG. 2, a plurality of microtransponders 100 are added to a sample 202. In the example system 200, the plurality of microtransponders 100 may be used for example, for a multiplex assay containing multiple nucleic acid targets. Also, the sample 202 and the microtransponders 100 may be added (e.g., via a pipette or other delivery mechanism) to a microchip, which is processed in a diagnostic component or device 204.

Figure 2:
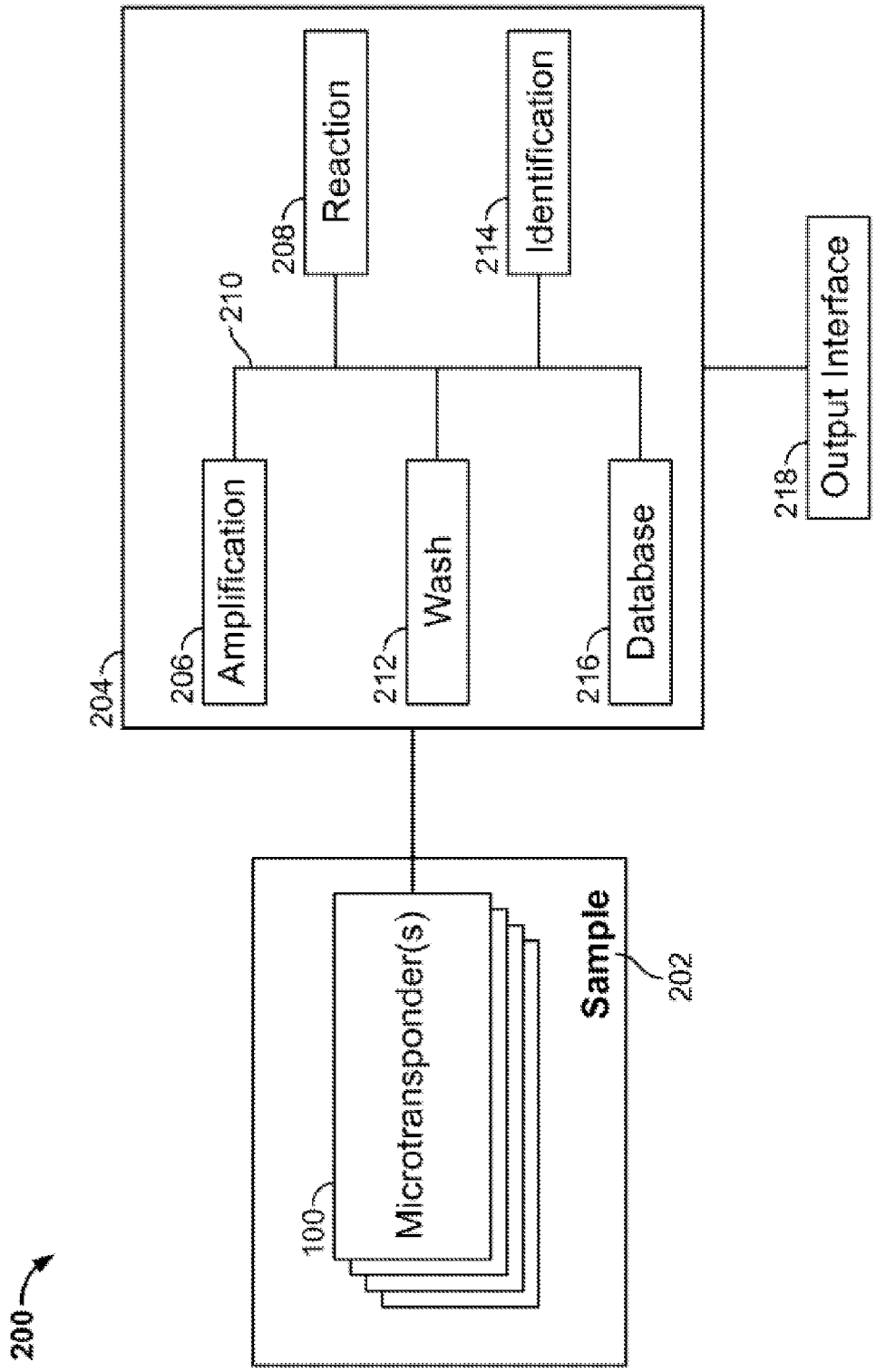
FIG. 2 is a block diagram of an example system for sequencing nucleic acids using the example microtransponder of FIG. 1.

The example diagnostic component 204 includes several stations, which are illustrated in FIG. 2 as discrete stations, but may be integral components. The diagnostic component 204 includes an amplification station 206. The nucleic acid target is clonally amplified on the surface of the microtransponder 100 at the amplification station 206. In some examples, the amplification is achieved through emulsion polymerase chase reaction. The amplified targets form surface-bound clonal targets.

The example system 200 also includes a reaction station 208. The microtransponder 100 is transported from the amplification station 206 to the reaction station 208, where the stations are positioned in different physical locations, through a transport mechanism 210 including, for example, a robotic arm, a microfluidic capillary or any other transport mechanism(s). At the reaction station 208, the surface-bound clonal targets are subject to a polymerization reaction (SBS) or a ligation reaction (SBL) to add a first labeled nucleotide base. If the nucleotide base to which the target is exposed during the SBS or SBL reaction is complementary to a first nucleotide base in a sequence of the nucleic acid target, the labeled nucleotide base binds with the target. Thus, if the first nucleotide base of the captured target is A, a labeled (e.g., fluorescently dyed) T will pair with the A. Every microtransponder 100 in the sample that has A as the first nucleotide base of the captured target has a T bound to the A. If the first nucleotide base of the target is not complementary with the nucleotide base presented during the SBS or SBL reaction, the microtransponder 100 and captured target proceed with no added base. In some examples, the added labeled nucleotide base is a set of labeled nucleotide bases. Also, the label may be an optical label, a fluorescent dye, a radioactive label and/or an electrochemical label. In some examples, a single type of label is used for a plurality of nucleotide bases. However, in other examples, different types of labels (e.g., different colors) are used to differentiate different nucleotide bases. In some examples, labeled nucleotide bases are added as single bases. However, in other examples, labeled nucleotide bases are added as an oligonucleotide. Oligonucleotides may include a number of nucleotide bases such as, for example, about thirty nucleotide bases.

The example system 200 includes a wash station 212 that is used to remove any extraneous polymerization reagent resulting from the polymerization reaction or an extraneous ligation reagent resulting from the ligation reaction. Each microtransponder 100 is left with the capture target and a first complementary, labeled nucleotide base of the sequence, if the added labeled nucleotide base was complementary with the first nucleotide base of the target. As noted above, if the labeled nucleotide base was not complementary with the first nucleotide base of the target, microtransponders 100 with such targets proceed with no added nucleotide base.

The example system 200 also includes an identification station 214 to determine an identity of the first nucleotide base in the sequence of the nucleic acid target. In some examples, the identification station 214 is a flow reader or meter that reads signals transmitted by the antenna 104 to detect, for example, a digital 1 or 0, representing a yes/no indicative of the presence/absence of the label. In some examples, the flow reader detects a presence or absence of the fluorescence or other color to determine whether the nucleotide base introduced at the reaction station 208 bounded to the first nucleotide base of the captured target. Also, in some examples, the flow reader can determine an intensity of the color. If, for example, the first two nucleotide bases of the captured target are the same, and the labeled nucleotide base introduced at the reaction station 208 is complementary, two of the introduced labeled nucleotide bases bind in sequence to the target. The intensity of the detectable color is doubled because two nucleotide bases with labels are bound. For example, if the target contains two sequential Ts, and the reaction station 208 introduces As to the sample, two As bind with the first two Ts. The identification station 214 detects a peak fluorescence that is double the fluorescence for a single joined A base.

In some examples, chain-terminating nucleotides are used. In such examples, one nucleotide base is added as a complementary base pair to the target sequence and the reaction stops. The added nucleotide is identified and the process may be repeated to add a subsequent nucleotide base. In these examples, four labels for the four types of nucleotide bases may be used, and the sample may be exposed to all four (or some combination of the four) nucleotide bases at the same time. The different labels can be discerned by the identification station 214 to determine which nucleotide base was added to which microtransponder 100.

The identification station 214 also detects the identification or transponder number associated with the identification tag 102 of the microtransponder 100, which is transmitted from the antenna 104. The digital signal representing the presence or absence of the nucleotide is matched with the microtransponder number. The microtransponder number is kept in a database 216 with the first nucleotide base of the target sequence, which is determined based on the complementary pair of the labeled nucleotide base that was added at the reaction station 208. If no nucleotide base was added during the reaction station 208, the identification station 214 reads the microtransponder number, but does not add a nucleotide base to the sequence stored in the database.

The example system 200 also includes an output interface 218 that may be, for example, a screen, other type of display and/or any suitable communication device. The output interface 218 may be used to display the nucleotide bases of the target sequence as the nucleotide bases are detected. Therefore, an operator of the system 200 can view the detection and identification of the target sequence in real time.

After the microtransponders 100 are sent through the identification station 214, the microtransponders 100 return to the reaction station 208 for mixing with a second introduced nucleotide base. The transport mechanism 210 may be used to transport the microtransponders 100 back to the reaction station 208. An additional nucleotide base is introduced to the sample. The second nucleotide base of the target, when complementary, binds with the additional labeled nucleotide when the first nucleotide base bound with the labeled nucleotide base of the first reaction. If the first nucleotide base of the target did not bind with the first labeled nucleotide base during the first reaction, the second labeled nucleotide base of the second reaction may bind with the first nucleotide base of the target, if complementary. If two of the first labeled nucleotide bases in the first reaction bind with the first two nucleotide bases of the target during the first reaction (where chain-terminating nucleotides were not used), the second labeled nucleotide base of the second reaction may bind with the third nucleotide base of the target, when complementary. In other words, during the second SBS or SBL reactions at the reaction station 208, a second type of labeled nucleotide base is introduced and binds to the target sequence at the next nucleotide base in the chain (whether that nucleotide base is the first, second, third, etc.) if complementary to the added labeled nucleotide base. Thus, a chain of the target sequence and complementary base pairs begin to form.

The operations at the wash station 212 and the identification station 214 are repeated, and the next sequence in the chains of the target is identified, stored in the database 216 and presented to the operator via the output interface 218. The microtransponders 100 are again reintroduced into the reaction station 208 for the introduction of yet another additional labeled nucleotide base. The process continues through the series of stations 208, 212, 214 a number of times (e.g., n times) until the target sequence is identified. The n number of cycles may be based on the number of nucleotides in the sequence of the nucleic acid target. In some examples, the n number of times the operations are repeated may correspond to an end of substantially an entire sequence.

While an example manner of implementing an example system 200 to identify a nucleic acid sequence has been illustrated in FIG. 2, one or more of the elements, processes and/or devices illustrated in FIG. 2 may be combined, divided, re-arranged, omitted, eliminated and/or implemented in any other way. Further, one or more portions of one or more of the example microtransponder(s) 100, the example diagnostic component 204, the example amplification station 206, the example reaction station 208, the example wash station 212, the example identification station 214, the example database 216, the example output interface 218 and/or, more generally, the example system 200 of FIGS. 1 and 2 may be implemented by hardware, software, firmware and/or any combination of hardware, software and/or firmware. Thus, for example, any of one or more portions of one or more of the example microtransponder(s) 100, the example diagnostic component 204, the example amplification station 206, the example reaction station 208, the example wash station 212, the example identification station 214, the example database 216, the example output interface 218 and/or, more generally, the example system 200 of FIGS. 1 and 2 could be implemented by one or more circuit(s), programmable processor(s), application specific integrated circuit(s) (ASIC(s)), programmable logic device(s) (PLD(s)) and/or field programmable logic device(s) (FPLD(s)), etc. Further still, the example system 200 of FIG. 2 may include one or more elements, processes and/or devices in addition to, or instead of, those illustrated in FIG. 2, and/or may include more than one of any or all of the illustrated elements, processes and devices.

Figure 3:
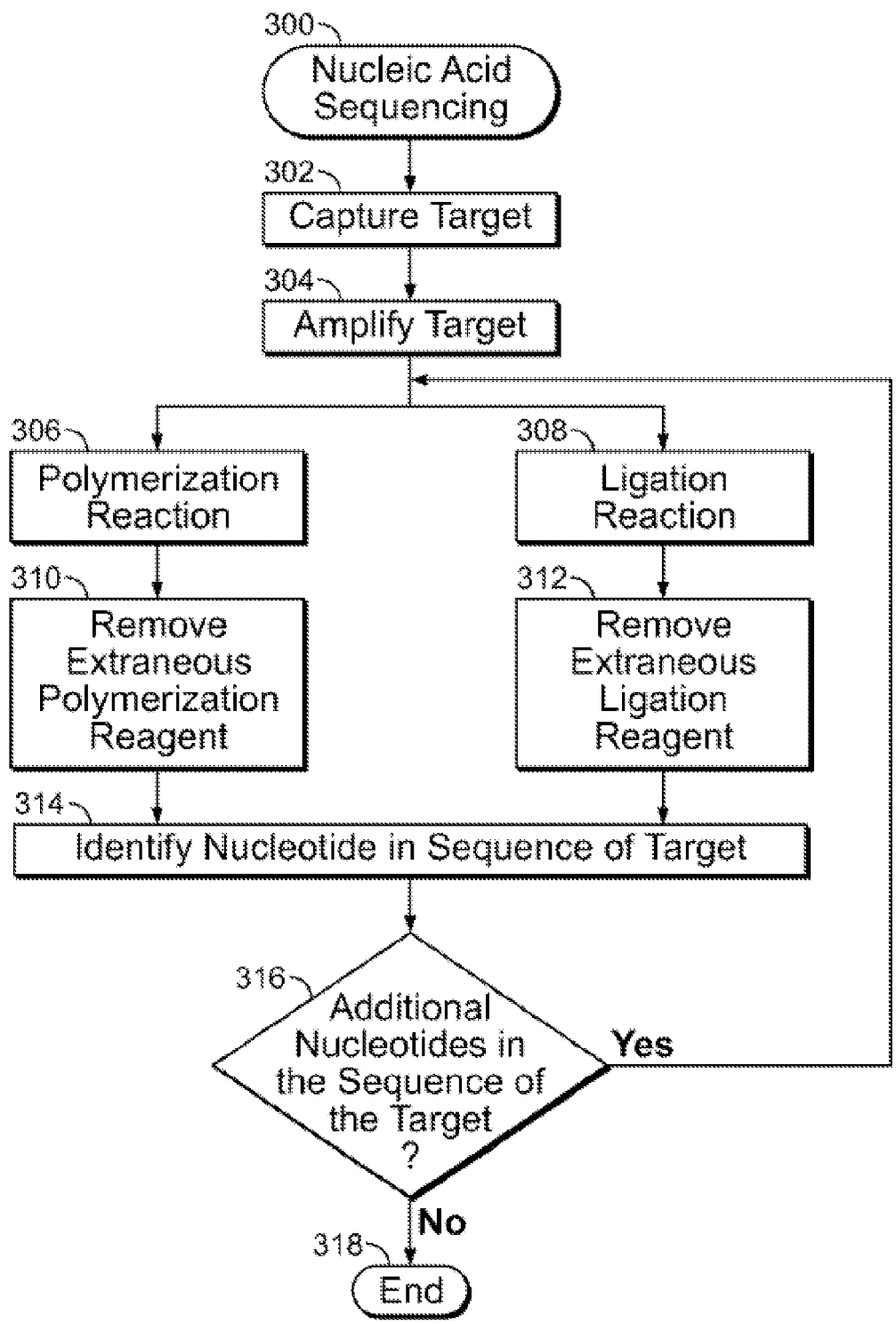
FIG. 3 is a flow chart representative of an example method that may be used to implement example systems disclosed herein.
Figure 4:
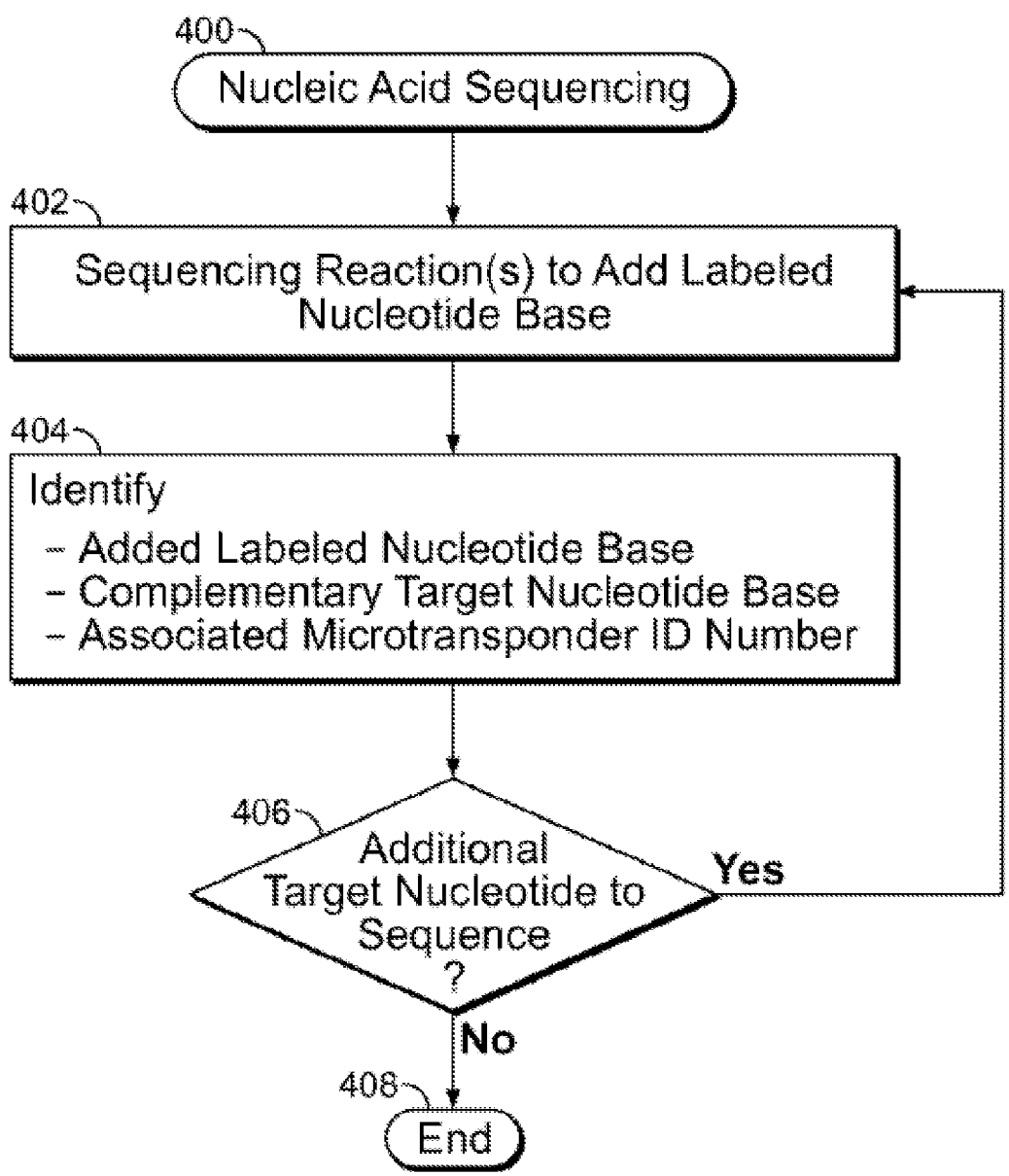
FIG. 4 is a flow chart representative of an example method that may be used to implement example systems disclosed herein.

Flowcharts representative of an example method for implementing the apparatus and systems of FIGS. 1 and 2 are shown in FIGS. 3 and 4. In this example, the method may be implemented using a program for execution by a processor such as the processor 512 shown in the example computer 500 discussed below in connection with FIG. 5. The program may be embodied in software stored on a tangible computer readable medium such as a CD-ROM, a floppy disk, a hard drive, a digital versatile disk (DVD), a Blu-ray disk, or a memory associated with the processor 512, but the entire program and/or parts thereof could alternatively be executed by a device other than the processor 512 and/or embodied in firmware or dedicated hardware. Further, although the example program is described with reference to the flowcharts illustrated in FIGS. 3 and 4, many other methods of implementing the example system 200 may alternatively be used. For example, the order of execution of the blocks may be changed, and/or some of the blocks described may be changed, eliminated, or combined.

As mentioned above, the example processes or methods of FIGS. 3 and 4 may be implemented using coded instructions (e.g., computer readable instructions) stored on a tangible computer readable medium such as a hard disk drive, a flash memory, a read-only memory (ROM), a compact disk (CD), a digital versatile disk (DVD), a cache, a random-access memory (RAM) and/or any other storage media in which information is stored for any duration (e.g., for extended time periods, permanently, brief instances, for temporarily buffering, and/or for caching of the information). As used herein, the term tangible computer readable medium is expressly defined to include any type of computer readable storage and to exclude propagating signals. Additionally or alternatively, the example methods of FIGS. 3 and 4 may be implemented using coded instructions (e.g., computer readable instructions) stored on a non-transitory computer readable medium such as a hard disk drive, a flash memory, a read-only memory, a compact disk, a digital versatile disk, a cache, a random-access memory and/or any other storage media in which information is stored for any duration (e.g., for extended time periods, permanently, brief instances, for temporarily buffering, and/or for caching of the information). As used herein, when the phrase "at least" is used as the transition term in a preamble of a claim, it is open-ended in the same manner as the term "comprising" is open ended. Thus, a claim using "at least" as the transition term in its preamble may include elements in addition to those expressly recited in the claim.

FIG. 3 illustrates a method 300 of sequencing a nucleic acid. The example method 300 includes the capture of a target nucleic acid sequence (block 302) on, for example, a surface of a microtransponder (e.g., the microtransponder 100 of FIG. 1). The example method 300 also includes amplifying the target nucleic acid sequence (block 304) via, for example, a polymerase chain reaction (e.g., at the amplification station 206 of FIG. 2).

In addition, the example method 300 includes a reaction of the target sequence with an added nucleotide base such as, for example, a labeled nucleotide base (blocks 306, 308). The reactions could be a polymerization reaction (block 306) such as, for example, SBS or a ligation reaction (block 308) such as, for example, SBL. The reactions may occur, for example, at the reaction station 208 of FIG. 2. The reactions enable a labeled nucleotide base to bind with a nucleotide base of the target nucleic acid sequence to form the next base pair of the target nucleic acid chain, as disclosed above. When the reaction is a polymerization reaction, the example method 300 includes removing extraneous polymerization reagent (block 310), and when the reaction is a ligation reaction, the example method 300 includes removing extraneous ligation reagent (block 312). The extraneous reagent removal may occur, for example at the wash station 212 of FIG. 2.

The example method 300 also includes identifying a nucleotide base in the target sequence (block 314). The identification determines, based on the detected label of an added nucleotide base and the identification/microtransponder number, what nucleotide base was added to what microtransponder surface. Because of the restrictive nature of base pairing (each type of nucleotide base only binds with one or type of nucleotide base), knowing what nucleotide base was added to the microtransponder leads to identification of nucleotide base is in the target nucleic acid sequence. A record may be kept (e.g., in the example database 216 of FIG. 2), to chart what nucleotide bases are added to what chain of the target sequences, and the results of what nucleotide bases are added may be presented to an operator in real time, i.e., as the chains of base pairs of added nucleotide bases and the target sequence are built.

The example method 300 determines if additional nucleotide bases in the target are to be added (block 316). If there are additional nucleotide bases to sequence, the example method 300 returns to the reaction at either bock 306 (for polymerization) or block 308 (for ligation). The example method 300 continues to add and identify the next nucleotide in the sequence. The method 300 repeats as necessary n number of times until all or substantially all of the target sequence has been identified. Then, if there are no more nucleotide bases to sequence (block 316), the example process ends (block 318). At the end of the method 300 all or substantially all of a target nucleic acid has been identified.

FIG. 4 illustrates another example method 400 of sequencing a nucleic acid. The example method 400 includes a plurality of sequencing reactions to which a sequence of target nucleotide bases captured on one or more microtransponders are subjected (block 402). In this example, the microtransponders may be, for example, the microtransponders 100 of FIGS. 1 and 2. Also, the sequencing reactions may be, for example, SBS or SBL, as disclosed above and may occur, for example, at the reaction station 208 of FIG. 2. In the example method 400, the sequencing reactions build a sequence of labeled nucleotide bases that are complementary to and bound to the sequence of target nucleotide bases.

The example method 400 also includes identifying each labeled nucleotide base of the sequence of labeled nucleotide bases (i.e., added labeled nucleotide bases) and each respective complementary target nucleotide base of sequence of target nucleotide bases to which the labeled nucleotide base is bound after each sequencing reaction (block 404). The identification portion of the example method 400 also reads an identification number of the microtransponder (block 404). In this example, the identification at block 404 may occur in the identification station 214 of FIG. 2, and the identification number of the microtransponder may be read from the identification tag 102 of the microtransponder 100 of FIG. 1. Also, each labeled nucleotide base of the sequence of labeled nucleotide bases and each respective complementary target nucleotide base of sequence of target nucleotide bases to which the labeled nucleotide base is bound may be associated with the identification number of the microtransponder. The identification(s) may be output to an operator as disclosed above.

The example method 400 of FIG. 4 also determines if there are additional target nucleotide bases to sequence (block 406). If there are additional target nucleotide bases to sequence, control returns to block 402 for subsequent sequencing reaction(s) to add additional labeled nucleotide bases. The method 400 then continues through subsequent identification (block 404). In some examples, each added labeled nucleotide base is identified between each subsequent sequencing reaction. If there are not additional target nucleotide bases to sequence (block 406), the example method ends (block 408).

Figure 5:
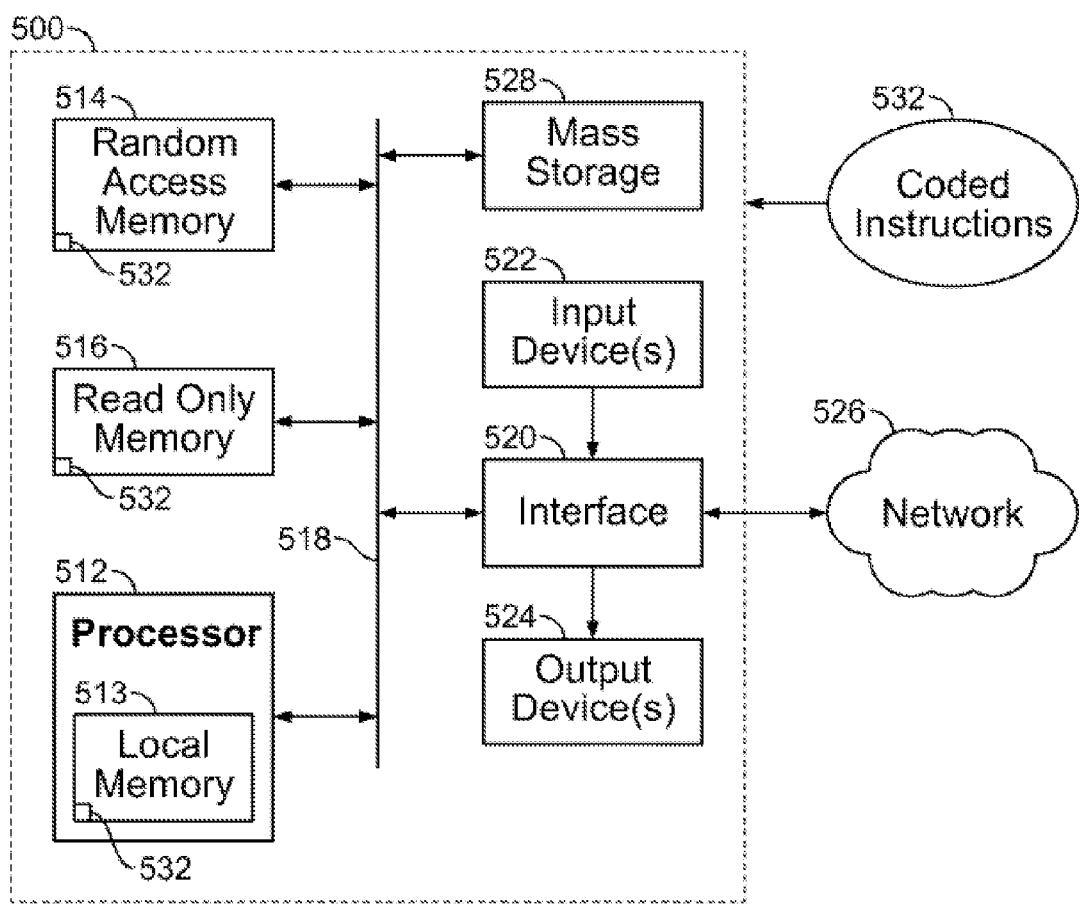
FIG. 5 illustrates an example processor platform that may execute instructions to perform the method of FIGS. 3 and/or 4 and/or, more generally, to implement any or all of the example methods, systems and/or apparatus disclosed herein.

FIG. 5 is a block diagram of an example computer 500 capable of executing the methods of FIGS. 3 and 4 to implement the system 200 FIG. 2. The computer 500 can be, for example, a server, a personal computer, or any other type of computing device.

The computer 500 of the instant example includes a processor 512. For example, the processor 512 can be implemented by one or more microprocessors or controllers from any desired family or manufacturer.

The processor 512 includes a local memory 513 (e.g., a cache) and is in communication with a main memory including a volatile memory 514 and a non-volatile memory 516 via a bus 518. The volatile memory 514 may be implemented by Synchronous Dynamic Random Access Memory (SDRAM), Dynamic Random Access Memory (DRAM), RAMBUS Dynamic Random Access Memory (RDRAM) and/or any other type of random access memory device. The non-volatile memory 516 may be implemented by flash memory and/or any other desired type of memory device. Access to the main memory 514, 516 is controlled by a memory controller.

The computer 500 also includes an interface circuit 520. The interface circuit 520 may be implemented by any type of interface standard, such as an Ethernet interface, a universal serial bus (USB), and/or a PCI express interface.

One or more input devices 522 are connected to the interface circuit 520. The input device(s) 522 permit a user to enter data and commands into the processor 512. The input device(s) can be implemented by, for example, a keyboard, a mouse, a touchscreen, a track-pad, a trackball, isopoint and/or a voice recognition system.

One or more output devices 524 are also connected to the interface circuit 520. The output devices 524 can be implemented, for example, by display devices (e.g., a liquid crystal display, a cathode ray tube display (CRT), a printer and/or speakers). The interface circuit 520, thus, typically includes a graphics driver card.

The interface circuit 520 also includes a communication device such as a modem or network interface card to facilitate exchange of data with external computers via a network 526 (e.g., an Ethernet connection, a digital subscriber line (DSL), a telephone line, coaxial cable, a cellular telephone system, etc.).

The computer 500 also includes one or more mass storage devices 528 for storing software and data. Examples of such mass storage devices 528 include floppy disk drives, hard drive disks, compact disk drives and digital versatile disk (DVD) drives.

The coded instructions 532 of FIG. 5 may be stored in the mass storage device 528, in the volatile memory 514, in the non-volatile memory 516, and/or on a removable storage medium such as a CD or DVD.

From the foregoing, it will appreciated that the above disclosed methods, apparatus, systems and articles of manufacture can be used to identify unknown nucleic acid sequences such as, for example, those sequences associated with the DNA of pathogens or genetic disorders, which may be used in the diagnosis of diseases. The examples disclosed here may be used to simultaneously determine the nucleic acid sequence of a plurality of targets at a high throughput rate with low processing and storage requirements. In addition, the examples disclosed herein provide real-time identification of the unknown targets to an operator as the nucleic acid(s) are sequenced.

Although certain example methods, apparatus and articles of manufacture have been described herein, the scope of coverage of this patent is not limited thereto. On the contrary, this patent covers all methods, apparatus and articles of manufacture fairly falling within the scope of the claims of this patent.

What is claimed is:

1. A method comprising: subjecting a sequence of target nucleotide bases captured on a microtransponder to a plurality of sequencing-by-synthesis reactions to sequentially add a sequence of single nucleotide bases that are complementary to and bound to the sequence of target nucleotide bases; identifying each added nucleotide base after each sequencing reaction; and associating each added nucleotide base of the sequence with an identification number of the microtransponder.

2. The method of claim 1, wherein the target nucleotide bases are captured via a capture probe.

3. The method of claim 1, wherein the target nucleotide bases comprise DNA or RNA.

4. The method of claim 1 further comprising clonally amplifying the target nucleotide bases.

5. The method of claim 4, wherein said clonally amplifying comprises an emulsion polymerase chain reaction prior to the sequencing reaction.

6. The method of claim 1, wherein at least one of the added nucleotide bases comprises a label.

7. The method of claim 6 wherein a single label is used for a plurality of added nucleotide bases.

8. The method of claim 6 wherein a plurality of different labels is used for each added nucleotide base to differentiate different added nucleotide bases.

9. The method of claim 1, wherein at least one of the added nucleotide bases comprises an optical label.

10. The method of claim 1, wherein at least one of the added nucleotide bases comprises an electrochemical label.

11. The method of claim 1, wherein identifying the added nucleotide base comprises detecting the added nucleotide base by employing a flow meter.

12. The method of claim 11, wherein said identifying comprises moving said microtransponder with said added base from a reaction station of an apparatus to an identification station of said apparatus using said flow meter.

13. The method of claim 12, wherein said identification station comprises a detector for detecting said added base, wherein said detector detects one or more of an optical signal, an electrical signal, and a chemical signal.

14. The method of claim 13, wherein said added base is detected by a change in fluorescence, luminescence, pH, heat, hydrogen ion concentration, pyrophosphate concentration, and radioactivity.

15. The method of claim 1 further comprising using a plurality of microtransponders for a multiplex assay containing more than one nucleic acid target.

16. The method of claim 1 further comprising performing at least a portion of the method in a microfluidic chip device.

17. A method comprising: subjecting a sequence of target nucleotide bases captured on a microtransponder to a plurality of sequencing-by-synthesis reactions to sequentially add a sequence of single nucleotide bases that are complementary to and bound to the sequence of target nucleotide bases;

moving said microtransponder with each added nucleotide base from a reaction station of an apparatus to an identification station of said apparatus using a flow meter;

identifying each added nucleotide base after each sequencing reaction; and moving said microtransponder from said identification station of said apparatus to said reaction station of said apparatus.

18. The method of claim 17 further comprising removing an extraneous sequencing reagent.

* * * * *